(12) United States Patent
Walker et al.

(10) Patent No.: US 7,074,894 B2
(45) Date of Patent: Jul. 11, 2006

(54) ANTIGEN COMPOSITION AGAINST MYCOPLASMA

(75) Inventors: John Walker, Balwyn (AU); Rogan Lee, Chapel Hill (AU); Stephen William Doughty, Blackburn (AU)

(73) Assignee: The University of Melbourne, Parkville (AU)

( * ) Notice: Subject to any disclaimer, the term of this patent is extended or adjusted under 35 U.S.C. 154(b) by 0 days.

(21) Appl. No.: 08/913,430

(22) PCT Filed: Mar. 15, 1996

(86) PCT No.: PCT/AU96/00149

§ 371 (c)(1),
(2), (4) Date: Dec. 9, 1997

(87) PCT Pub. No.: WO96/28472

PCT Pub. Date: Sep. 19, 1996

(65) Prior Publication Data

US 2003/0092897 A1 May 15, 2003

(30) Foreign Application Priority Data

Mar. 16, 1995 (AU) .................................. PN 1789

(51) Int. Cl.
*C07H 1/00* (2006.01)
*C07H 14/00* (2006.01)
*C07H 17/00* (2006.01)

(52) U.S. Cl. ...................... 530/350; 435/870; 530/806; 530/820; 530/821

(58) Field of Classification Search .................. 424/88, 424/92; 435/870; 530/350, 806, 820, 821
See application file for complete search history.

(56) References Cited

U.S. PATENT DOCUMENTS

| 4,894,332 A | 1/1990 | Schaller et al. ............ 435/69.3 |
| 5,240,706 A | 8/1993 | Faulds .......................... 424/92 |
| 5,252,328 A | 10/1993 | Faulds et al. .................. 424/92 |
| 5,641,638 A * | 6/1997 | Bredt et al. ................. 435/7.32 |

FOREIGN PATENT DOCUMENTS

| AU | 7068587 | 10/1987 |
| AU | 4903590 | 10/1990 |
| AU | 1760295 | 10/1995 |
| EP | 0475185 | 3/1992 |
| EP | 0571648 | 12/1993 |
| WO | 9007935 | 7/1990 |
| WO | 9115593 | 10/1991 |

OTHER PUBLICATIONS

Futo, S., et al. "Molecular Cloning of a 46-Kilodalton Surface Autigen (P46) Gene from Mycoplasma Hyopneumoniae: Direct Evidence of CGG Codon Usage for Arginine", *Journal of Bacteriology*, 1995, pp. 1915-1917.

Futo, S., et al. "Recombinant 46-Kilodalton Surface Antigen (P46) of Mycoplasma hyopneumoniae Expressed in *Escherichia coli* Can Be Used for Early Specific Diagnosis of Myoplasmal Pneumonia of Swine by Enzyme Linked Immunosorbent Assay", *Journal of Clinical Microbiology*, Mar. 1995, pp. 680-683.

Klinkert, M., et al., Surface Proteins of Mycoplasma hyopneumoniae Identified from an *Escherichia coli* Expression Plasmid Library, *Infection and Immunity*, Aug. 1995, pp. 329-335.

Derwent Abstract of JP 62-273455 of Nov. 1987.
Derwent Abstract of JP 02-167, 079 of Jun. 1990.
Derwent Abstract of JP 07-118167 of May, 1995.

Etheridge, J.R., "Isolation of Mycoplasma Hyopneumoniae From Lesions In Experimentally Infected Pigs", *Australian Veterinary Journal*, vol. 55, Aug. 1979, pp. 356-359.

Bordier, C., "Separation of Integral Membrane Proteins in Trinton X-114", *Journal of Biochemical Chemistry*, Feb. 1981, pp. 1604-1607.

Holton, T., et al., "Simple and efficient method for direct cloning of PCR products using ddT-tailed vectors", Nucleic Acids Research, vol. 19, No. 5, Dec. 1990, p. 1156.

Hovind-Hougen, K., Friss, N.F., Research in Veterinary Science, 1991, 51, pp. 155-163, "Morphological & Ultrastructural Studies in M flocculare and M hyopneumoniae in vitro".

Warren H.S. and Chedid, L.A., Future Prospects for Vaccine Adjuvants CRC Critical Review in Immunology 8:83-108, 1988.

A monoclonal blocking ELISA detecting serum antibodies to *Mycoplasma hyopneumoniae*, Niels, Fred, et al Veterinary Microbiology 30 (1992) 35-46.

Immunological and pathological reactions in piglets experimentally infected with *Mycoplasma hyopneumoniae* and/or *Mycoplasma flocculare*, Strasser, M. et al Veterinary Immunology and Immunopathology, 31 (1992) 141-53.

Species-specific Antigens of *Mycoplasma hyopneumoniae* and Cross-reactions with Other Porcine Mycoplasmas, Bolske, Goran, et al Current Microbiology, 15 (1987) 233-239.

* cited by examiner

Primary Examiner—Rodney P Swartz
(74) *Attorney, Agent, or Firm*—Ladas & Parry LLP

(57) ABSTRACT

An isolated antigen against a *Mycoplasma*, prepared by a method including providing a sample of a *Mycoplasma* and an antibody probe, probing the *Mycoplasma* sample with the antibody probe to detect at least one antigen, and isolating the antigen detected. The antibody probe includes at least one antibody against the *Mycoplasma* that is produced by a method including (a) providing a biological sample taken a short time after an immune animal has been challenged with a *Mycoplasma* or *Mycoplasma* extract taken from the infection site or an area of a lesion or an area close to the infection site or lesion; (b) isolating cells from the biological sample; (c) culturing the cells in vitro in a suitable culture medium; and (d) harvesting antibodies produced from the cell.

18 Claims, 4 Drawing Sheets

Figure 1:
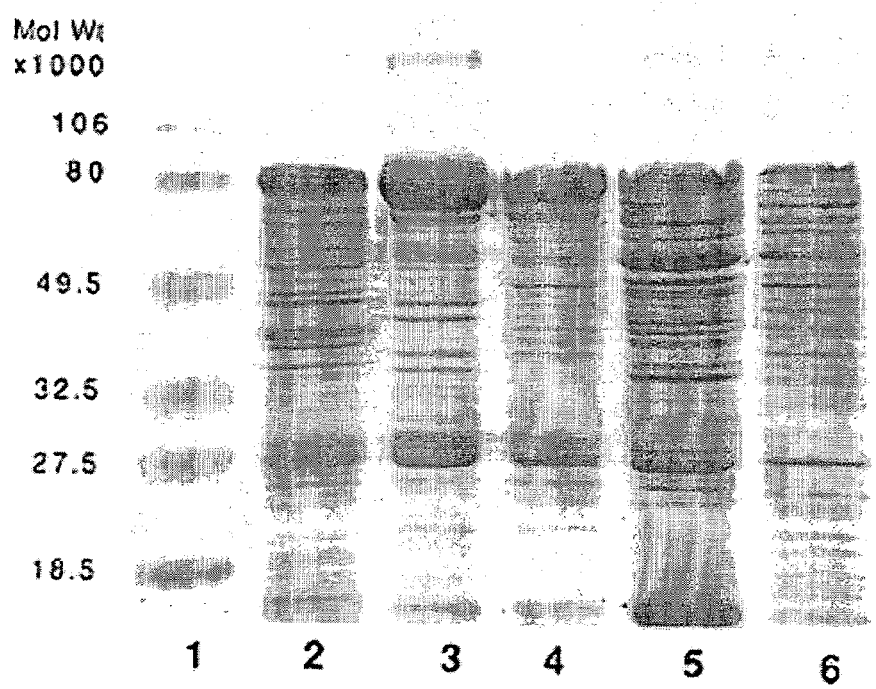

|  | 10 | 20 | 30 | 40 | 50 |  |
|---|---|---|---|---|---|---|
|  | 1234567890 | 1234567890 | 1234567890 | 1234567890 | 1234567890 |  |
|  | ATGAAAAAAA | TGCCACTATA | CCAGAGGAAA | GAGCAGTATA | TAAAATAATT | 50 |
|  | AAAATTACAT | TTTCTTCATT | TGCGCCAGAA | TTTTTAAGAA | TTAGTACATT | 100 |
|  | AAAAAGTAGA | ACAAAAGTTA | TTAATGTAAA | CATTAGCGCA | ATCCTTAAGA | 150 |
|  | AAAAATTAAA | AGTTTTATCT | ATTTTTTTTA | ATCGAAATCC | AACCAGGCAT | 200 |
|  | AAATCTTTGT | CAGTATTTAT | CAAGTCGGTA | TTTTTTCATT | ATTTCTACTA | 250 |
|  | AAATATTATT | TGAATTGCA | TTTTCCATAA | TCTAAAATTT | TACATTTTTT | 300 |
|  | TATAACAATT | TTTAAAATT | ACTCTTTAAT | TTATAGTATT | TTTTTATTTT | 350 |
|  | TTAGTCTAAA | TTATAAAATT | ATCTTGAATT | TTATTTGAAT | TTTTATAATT | 400 |
|  | TAGTACTAAA | AAATACAAAT | ATTTTTTCCT | ATTCTAAGAA | AAATTCATTT | 450 |
|  | TTTAAAAAAA | ATTGATTTTT | ATAGTATAAT | TTGTTTGTAT | AATTGAATTA | 500 |
|  | ACTTGATTTG | AAAGGGAACA | AAATGAAAAA | AATGCTTAGA | AAAAAATTCT | 550 |
|  | TGTATTCATC | AGCTATTTAT | GCAACTTCGC | TTGCATCAAT | TATTGCATTT | 600 |
|  | GTTGCAGCAG | GTTGTGGACA | GACAGAATCA | GGTTCAACTT | CTGATTCTAA | 650 |
|  | ACCACAAGCC | GAGACGCTAA | AACATAAAGT | AAGTAATGAT | TCTATTCGAA | 700 |
|  | TAGCACTAAC | CGATCCGGAT | AATCCTCGAT | GAATTAGTGC | CCAAAAAGAT | 750 |
|  | ATTATTTCTT | ATGTTGATGA | AACAGAGGCA | GCAACTTCAA | CAATTACAAA | 800 |
|  | AAACCAGGAT | GCACAAAATA | ACTGACTCAC | TCAGCAAGCT | AATTAAGCC | 850 |
|  | CAGCGCCAAA | AGGATTTATT | ATTGCCCCTG | AAAATGGAAG | TGGAGTTGGA | 900 |
|  | ACTGCTGTTA | ATACAATTGC | TGATAAAGGA | ATTCCGATTG | TTGCCTATGA | 950 |
|  | TCGACTAATT | ACTGGATCTG | ATAAATATGA | TTGGTATGTT | TCTTTTGATA | 1000 |
|  | ATGAAAAAGT | TGGTGAATTA | CAAGGTCTTT | CACTTGCTGC | GGGTCTATTA | 1050 |
|  | GGAAAAGAAG | ATGGTGCTTT | TGATTCAATT | GATCAAATGA | ATGAATATCT | 1100 |
|  | AAAATCACAT | ATGCCCCAAG | AGACAATTTC | TTTTTATACA | ATCGCGGGTT | 1150 |
|  | CCCAAGATGA | TAATAATTCC | CAATATTTTT | ATAATGGTGC | AATGAAAGTA | 1200 |
|  | CTTAAAGAAT | TAATGAAAAA | TTCGCAAAAT | AAAATAATTG | ATTTATCTCC | 1250 |
|  | TGAAGGCGAA | AATGCTGTTT | ATGTCCCAGG | ATGAAATTAT | GGAACTGCCG | 1300 |
|  | GTCAAAGAAT | CCAATCTTTT | CTAACAATTA | ACAAAGATCC | AGCAGGTGGT | 1350 |
|  | AATAAAATCA | AAGCTGTTGG | TTCAAAACCA | GCTTCTATTT | TCAAAGGATT | 1400 |
|  | TCTTGCCCCA | AATGATGGAA | TGGCCGAACA | AGCAATCACC | AAATTAAAAC | 1450 |
|  | TTGAAGGGTT | TGATACCCAA | AAAATCTTTG | TAACTCGTCA | AGATTATAAT | 1500 |
|  | GATAAAGCCA | AAACTTTTAT | CAAAGACGGC | GATCAAAATA | TGACAATTTA | 1550 |
|  | TAAACCTGAT | AAAGTTTTAG | GAAAAGTTGC | TGTTGAAGTT | CTTCGGGTTT | 1600 |
|  | TAATTGCAAA | GAAAAATAAA | GCATCTAGAT | CAGAAGTCGA | AAACGAACTA | 1650 |
|  | AAAGCAAAAC | TACCAAATAT | TTCATTTAAA | TATGATAATC | AAACATATAA | 1700 |
|  | AGTACAAGGT | AAAAATATTA | ATACAATTTT | AGTAAGTCCA | GTAATTGTTA | 1750 |
|  | CAAAAGCTAA | TGTTGATAAT | CCTGATGCCT | AA |  | 1782 |

FIG. 6

```
              10         20         30         40         50
      1234567890 1234567890 1234567890 1234567890 1234567890

MKKMLRKKFL YSSAIYATSL ASIIAFVAAG CGQTESGSTS DSKPQAETLK    50
      HKVSNDSIRI ALTDPDNPRW ISAQKDIISY VDETEAATST ITKNQDAQNN   100
      WLTQQANLSP APKGFIIAPE NGSGVGTAVN TIADKGIPIV AYDRLITGSD   150
      KYDWYVSFDN EKVGELQGLS LAAGLLGKED GAFDSIDQMN EYLKSHMPQE   200
      TISFYTIAGS QDDNNSQYFY NGAMKVLKEL MKNSQNKIID LSPEGENAVY   250
      VPGWNYGTAG QRIQSFLTIN KDPAGGNKIK AVGSKPASIF KGFLAPNDGM   300
      AEQAITKLKL EGFDTQKIFV TRQDYNDKAK TFIKDGDQNM TIYKPDKVLG   350
      KVAVEVLRVL IAKKNKASRS EVENELKAKL PNISFKYDNQ TYKVQGKNIN   400
      TILVSPVIVT KANVDNPDA                                     419
```

FIG. 7

ANTIGEN COMPOSITION AGAINST MYCOPLASMA

The present invention relates to protective and diagnostic antigens, the preparation thereof, and their use in the formation of vaccine compositions, particularly vaccine compositions against *Mycoplasma hyopneumoniae* infections.

*Mycoplasma hyopneumoniae* is a ubiquitous swine respiratory pathogen causing mycoplasmal pneumoniae in swine (swine enzootic pneumonia). Swine enzootic pneumonia is probably the most widespread and economically significant disease in swine producing countries of the world. The economic effects of swine enzootic pneumonia (SEP) are complex, and the cost of the disease is severe. In Australia, the disease was estimated in 1988 to cost approximately $20,000,000 per annum. Increased mortality, decreased growth weight, depressed feed conversion, susceptibility to secondary bacterial infections, increased management costs, and increased use of antibiotics, are the main reasons for the economic impact of SEP.

Whilst several experimental vaccines have been produced, these have resulted in less than optimal results, and utilizing various classes of antibiotics such as tetracycline, lincamycin and tiamulin is still the most widespread control treatment. Such antibiotics are, however, of limited therapeutic value, because they do not prevent the establishment of an infection, and lung lesions may develop after treatment ends.

European Patent Application 359,919 to ML Technology Ventures L.P. describes a series of antigens, 36 kD, 41 kD, 74.5 kD and 96 kD in size, and proposes the use of such antigens in vaccines. Results presented suggest that some protection in pigs against challenge was achieved.

However, there remains a need in the art for an effective vaccine against *M. hyopneumoniae* which would confer protection against colonization and clinical disease following *M. hyopneumoniae* challenge and also significantly reduce the morbidity and mortality from secondary infections.

Accordingly, it is an object of the present invention to overcome, or at least alleviate, one or more of the difficulties and deficiencies in the prior art.

Accordingly, in a first aspect of the present invention there is provided a protective antigen against a *Mycoplasma*, preferably *Mycoplasma hyopneumoniae* prepared by a method including
  providing
  a sample of a *Mycoplasma*;
  an antibody probe including at least one antibody against a *Mycoplasma* produced by a method including;
    providing a biological sample taken a short time after an immune animal has been challenged with a *Mycoplasma* or *Mycoplasma* extract taken from the infection site or an area of a lesion or an area close to the infection site or lesion;
    isolating cells from the biological sample;
    culturing cells in vitro in a suitable culture medium; and
    harvesting antibodies produced from said cells;
  probing the *Mycoplasma* sample with the antibody probe to detect at least, one antigen; and
  isolating the antigen detected.

The protective antigens may also function as diagnostic antigens as discussed below.

Accordingly, in a preferred aspect of the present invention there is provided a putative protective antigen against *Mycoplasma hyopneumoniae*, or related infections, selected from antigens having approximate molecular weights of 110–114, 90–94, 72–75, 60–64, 52–54 and 46–48 kilodaltons (kD), as hereinafter described, mutants, derivatives and fragments thereof. The protective antigen may be a surface protein. The protective antigen may be a surface lipoprotein or membrane protein.

Preferably the protective antigens are selected from antigens having approximate molecular weights of 110–114, 90–94, 74, 62, 52 and 48 kD.

Preferably, the 72–75 kD antigen includes the following N-terminal amino acid sequence: (SEQ ID NO:12)
  AGXLQKNSLLEEVWYLAL and, optionally, one or more of the following internal amino acid sequences: (SEQ ID NO:13, SEQ ID NO:14 and SEQ ID NO:15 respectively)
  AKNFDFAPSIQGYKKIAHEL
  NLKPEQILQLLG
  LLKAEXNKXIEEINTXLDN Preferably, the 60–64 kD antigen includes one of the following N-terminal amino acid sequences: (SEQ ID NO:10 and SEQ ID NO:11 respectively)
  MKLAKLLKGFX(N/L)(M/V)IK
  ADP(F/I)(R/E)Y(V/A)PQG(Q/A)X(MIN)VG Preferably, the 52–54 kD antigen includes the following N-terminal amino acid sequence: (SEQ ID NO:7)
  AGXWAKETTKEEKS and, optionally, one or more of the following internal amino acid sequences: (SEQ ID NO:8, and SEQ ID NO:9 respectively)
  AWVTADGTVN
  AIVTADGTVNDNKPNQWVRKY.

Preferably, the 46–48 kD antigen includes the following N-terminal amino acid sequence: (SEQ ID NO:3)
  AGXGQTESGSTSDSKPQAETLKHKV and, optionally, one or more of the following internal amino acid sequences: (SEQ ID NO:4; SEQ ID NO:5; and SEQ ID NO:6 respectively)
  TIYKPDKVLGKVAVEVLRVLIAKKNKASR
  AEQAITKLKLEGFDTQ
  KNSQNKIIDLSPEG The 46–48 kD antigen may be encoded by a nucleic acid fragment: (SEQ ID NO:1)

```
         10         20         30         40         50
 1234567890 1234567890 1234567890 1234567890 1234567890

ATGAAAAAAA TGCCACTATA CCAGAGGAAA GAGCAGTATA TAAAATAATT    50

AAAATTACAT TTTCTTCATT TGCGCCAGAA TTTTTAAGAA TTAGTACATT   100

AAAAAGTAGA ACAAAAGTTA TTAATGTAAA CATTAGCGCA ATCCTTAAGA   150
```

-continued

```
         10         20         30         40         50
  1234567890 1234567890 1234567890 1234567890 1234567890

AAAAATTAAA AGTTTTATCT ATTTTTTTTA ATCGAAATCC AACCAGGCAT    200

AAATCTTTGT CAGTATTTAT CAAGTCGGTA TTTTTTCATT ATTTCTACTA    250

AAATATTATT TGAATTTGCA TTTTCCATAA TCTAAAATTT TACATTTTTT    300

TATAACAATT TTTAAAAATT ACTCTTTAAT TTATAGTATT TTTTTATTTT    350

TTAGTCTAAA TTATAAAATT ATCTTGAATT TTATTTGAAT TTTTATAATT    400

TAGTACTAAA AAATACAAAT ATTTTTTCCT ATTCTAAGAA AAATTCATTT    450

TTTAAAAAAA ATTGATTTTT ATAGTATAAT TTGTTTGTAT AATTGAATTA    500

ACTTGATTTG AAAGGGAACA AAATGAAAAA AATGCTTAGA AAAAAATTCT    550

TGTATTCATC AGCTATTTAT GCAACTTCGC TTGCATCAAT TATTGCATTT    600

GTTGCAGCAG GTTGTGGACA GACAGAATCA GGTTCAACTT CTGATTCTAA    650

ACCACAAGCC GAGACGCTAA AACATAAAGT AAGTAATGAT TCTATTCGAA    700

TAGCACTAAC CGATCCGGAT AATCCTCGAT GAATTAGTGC CCAAAAAGAT    750

ATTATTTCTT ATGTTGATGA AACAGAGGCA GCAACTTCAA CAATTACAAA    800

AAACCAGGAT GCACAAAATA ACTGACTCAC TCAGCAAGCT AATTTAAGCC    850

CAGCGCCAAA AGGATTTATT ATTGCCCCTG AAAATGGAAG TGGAGTTGGA    900

ACTGCTGTTA ATACAATTGC TGATAAAGGA ATTCCGATTG TTGCCTATGA    950

TCGACTAATT ACTGGATCTG ATAAATATGA TTGGTATGTT TCTTTTGATA   1000

ATGAAAAAGT TGGTGAATTA CAAGGTCTTT CACTTGCTGC GGGTCTATTA   1050

GGAAAAGAAG ATGGTGCTTT TGATTCAATT GATCAAATGA ATGAATATCT   1100

AAAATCACAT ATGCCCCAAG AGACAATTTC TTTTTATACA ATCGCGGGTT   1150

CCCAAGATGA TAATAATTCC CAATATTTTT ATAATGGTGC AATGAAAGTA   1200

CTTAAAGAAT TAATGAAAAA TTCGCAAAAT AAAATAATTG ATTTATCTCC   1250

TGAAGGCGAA AATGCTGTTT ATGTCCCAGG ATGAAATTAT GGAACTGCCG   1300

GTCAAAGAAT CCAATCTTTT CTAACAATTA ACAAAGATCC AGCAGGTGGT   1350

AATAAAATCA AAGCTGTTGG TTCAAAACCA GCTTCTATTT TCAAAGGATT   1400

TCTTGCCCCA AATGATGGAA TGGCCGAACA AGCAATCACC AAATTAAAAC   1450

TTGAAGGGTT TGATACCCAA AAAATCTTTG TAACTCGTCA AGATTATAAT   1500

GATAAAGCCA AAACTTTTAT CAAAGACGGC GATCAAAATA TGACAATTTA   1550

TAAACCTGAT AAAGTTTTAG GAAAAGTTGC TGTTGAAGTT CTTCGGGTTT   1600

TAATTGCAAA GAAAAATAAA GCATCTAGAT CAGAAGTCGA AAACGAACTA   1650

AAAGCAAAAC TACCAAATAT TTCATTTAAA TATGATAATC AAACATATAA   1700

AGTACAAGGT AAAAATATTA ATACAATTTT AGTAAGTCCA GTAATTGTTA   1750

CAAAAGCTAA TGTTGATAAT CCTGATGCCT AA                      1782
```

Accordingly, in a further aspect the present invention provides an isolated nucleic acid fragment encoding a putative protective antigen against *Mycoplasma hyopneumoniae* or related infections, said nucleic acid fragment: (SEQ ID NO:1)

|  |  |
|---|---|
| `         10         20         30         40         50` | |
| `1234567890 1234567890 1234567890 1234567890 1234567890` | |
| ATGAAAAAAA TGCCACTATA CCAGAGGAAA GAGCAGTATA TAAAATAATT | 50 |
| AAAATTACAT TTTCTTCATT TGCGCCAGAA TTTTTAAGAA TTAGTACATT | 100 |
| AAAAAGTAGA ACAAAAGTTA TTAATGTAAA CATTAGCGCA ATCCTTAAGA | 150 |
| AAAAATTAAA AGTTTTATCT ATTTTTTTTA ATCGAAATCC AACCAGGCAT | 200 |
| AAATCTTTGT CAGTATTTAT CAAGTCGGTA TTTTTTCATT ATTTCTACTA | 250 |
| AAATATTATT TGAATTTGCA TTTTCCATAA TCTAAAATTT TACATTTTTT | 300 |
| TATAACAATT TTTAAAAATT ACTCTTTAAT TTATAGTATT TTTTTATTTT | 350 |
| TTAGTCTAAA TTATAAAATT ATCTTGAATT TTATTTGAAT TTTTATAATT | 400 |
| TAGTACTAAA AAATACAAAT ATTTTTTCCT ATTCTAAGAA AAATTCATTT | 450 |
| TTTAAAAAAA ATTGATTTTT ATAGTATAAT TTGTTTGTAT AATTGAATTA | 500 |
| ACTTGATTTG AAAGGGAACA AAATGAAAAA AATGCTTAGA AAAAAATTCT | 550 |
| TGTATTCATC AGCTATTTAT GCAACTTCGC TTGCATCAAT TATTGCATTT | 600 |
| GTTGCAGCAG GTTGTGGACA GACAAAATCA GGTTCAACTT CTGATTCTAA | 650 |
| ACCACAAGCC GAGACGCTAA ACATAAAGT AAGTAATGAT TCTATTCGAA | 700 |
| TAGCACTAAC CGATCCGGAT AATCCTCGAT GAATTAGTGC CCAAAAAGAT | 750 |
| ATTATTTCTT ATGTTGATGA ACAGAGGCA GCAACTTCAA CAATTACAAA | 800 |
| AAACCAGGAT GCACAAAATA ACTGACTCAC TCAGCAAGCT AATTTAAGCC | 850 |
| CAGCGCCAAA AGGATTTATT ATTGCCCCTG AAAATGGAAG TGGAGTTGGA | 900 |
| ACTGCTGTTA ATACAATTGC TGATAAAGGA ATTCCGATTG TTGCCTATGA | 950 |
| TCGACTAATT ACTGGATCTG ATAAATATGA TTGGTATGTT TCTTTTGATA | 1000 |
| ATGAAAAAGT TGGTGAATTA CAAGGTCTTT CACTTGCTGC GGGTCTATTA | 1050 |
| GGAAAAGAAG ATGGTGCTTT TGATTCAATT GATCAAATGA ATGAATATCT | 1100 |
| AAAATCACAT ATGCCCCAAG AGACAATTTC TTTTTATACA ATCGCGGGTT | 1150 |
| CCCAAGATGA TAATAATTCC CAATATTTTT ATAATGGTGC AATGAAAGTA | 1200 |
| CTTAAAGAAT TAATGAAAAA TTCGCAAAAT AAAATAATTG ATTTATCTCC | 1250 |
| TGAAGGCGAA AATGCTGTTT ATGTCCCAGG ATGAAATTAT GGAACTGCCG | 1300 |
| GTCAAAGAAT CCAATCTTTT CTAACAATTA ACAAAGATCC AGCAGGTGGT | 1350 |
| AATAAAATCA AAGCTGTTGG TTCAAAACCA GCTTCTATTT TCAAAGGATT | 1400 |
| TCTTGCCCCA AATGATGGAA TGGCCGAACA AGCAATCACC AAATTAAAAC | 1450 |
| TTGAAGGGTT TGATACCCAA AAAATCTTTG TAACTCGTCA AGATTATAAT | 1500 |
| GATAAAGCCA AAACTTTTAT CAAAGACGGC GATCAAAATA TGACAATTTA | 1550 |
| TAAACCTGAT AAAGTTTTAG AAAAGTTGC TGTTGAAGTT CTTCGGGTTT | 1600 |
| TAATTGCAAA GAAAAATAAA GCATCTAGAT CAGAAGTCGA AAACGAACTA | 1650 |
| AAAGCAAAAC TACCAAATAT TTCATTTAAA TATGATAATC AAACATATAA | 1700 |
| AGTACAAGGT AAAATATTA ATACAATTTT AGTAAGTCCA GTAATTGTTA | 1750 |
| CAAAAGCTAA TGTTGATAAT CCTGATGCCT AA | 1782 |

As cross protection between various *Mycoplasma* such as *M. hyorhinis* and *M. synoviae* has been documented, similar antigens may also be detected in other *Mycoplasma* species (FIG. 1).

In a still further aspect the present invention provides a method for preventing *Mycoplasma* infection in animals. Preferably the *Mycoplasma* disease is a *Mycoplasma hyopneumoniae* disease such as swine enzootic pneumonia (SEP). This method includes administering to an animal an effective amount of at least one protective antigen against *Mycoplasma* as described above.

The present invention further provides a vaccine composition including a prophylactically effective amount of at least one protective antigen against a *Mycoplasma* as herein described. Preferably the veterinary composition includes two or more protective antigens as herein described.

Accordingly in a preferred aspect the present invention provides a vaccine composition including two or more protective antigens selected from antigens having approximate molecular weights of 110–114, 90–94, 72–75, 60–64, 52–54 and 46–48 kilodaltons.

The vaccine composition may include any combination of two or more protective antigens selected from antigens having approximate molecular weights of 110–114, 90–94, 72–75, 60–64, 52–54 and 46–48 kD. The two or more antigens may be selected from antigens falling within one of the specified approximate molecular weights and/or antigens from different specified approximate molecular weights. The composition may contain 3, 4, 5 or 6 antigens selected from protective antigens having molecular weights of approximately 110–114, 90–94, 72–75, 60–64, 52–54 and 46–48 kD.

The vaccine compositions according to the present invention may be administered orally or may be administered parenterally (for example by intramuscular, subcutaneous, intradermal or intravenous injection). The amount required will vary with the antigenicity of the active ingredient and need only be an amount sufficient to induce an immune response typical of existing vaccines.

Reactive experimentation will easily establish the required amount. Typical initial doses of vaccine or veterinary compositions may be approximately 0.001–1 mg active ingredient/kg body weight. The dose rate may increase or multiple doses may be used as needed to provide the desired level of protection.

The vaccine composition according to the present invention may further include a veterinary acceptable carrier, diluent or excipient therefor. Preferably the active ingredient may be suspended or dissolved in a carrier. The carrier may be any solid or solvent that is nontoxic to the animal and compatible with the active ingredient. Suitable carriers include liquid carriers, such as normal saline and other nontoxic salts at or near physiological concentrations, and solid carriers, such as talc or sucrose.

Preferably the vaccine contains an adjuvant, such as Freund's adjuvant, complete or incomplete, or immunomodulators such as cytokines may be added to enhance the antigenicity of the antigen if desired.

More preferably the adjuvant is of the mineral-oil type as these have been found to be consistently superior at inducing antibody titers and Delayed Type Hypersensitivity responses. A particularly preferred adjuvant is that marketed under the trade designation Montanide ISA-50 and available from Seppic, Paris, France.

When used for administering via the bronchial tubes, the vaccine is suitably present in the form of an aerosol.

In a still further aspect of the present invention there is provided a diagnostic kit including a diagnostic antigen against a *Mycoplasma*, preferably *Mycoplasma hyopneumoniae*, identified and purified as described above.

The protective antigens according to the present invention may be isolated and identified utilizing the general methods described in Australian patent application 49035/90, the entire disclosure of which is incorporated herein by reference.

Accordingly, in a further aspect, the present invention provides a method for producing at least one antibody against a *Mycoplasma*. This method includes
providing a biological sample taken a short time after an immune animal has been challenged with a *Mycoplasma* or *Mycoplasma* extract taken from the infection site or an area of a lesion or an area close to the infection site or lesion;
isolating cells from the biological sample;
culturing cells in vitro in a suitable culture medium; and
harvesting antibodies produced from said cells.

The *Mycoplasma* may be *Mycoplasma hyopneumoniae*.

The animal may be a mammal including humans. The mammal may be a domestic animal such as a pig, sheep or cattle.

The biological animal sample may be of any suitable type. The biological sample may be taken from animal tissue, organs, lymph or lymph nodes. The biological sample may be taken from the infection site, the lungs of the animal, or an area of a lesion which may be formed or an area close to the infected site or a lesion such as in the lymph nodes draining from the lungs.

However, serum/plasma samples are not used as the biological samples according to this aspect of the present invention. It has been found that the majority of antibodies found in a serum/plasma sample are irrelevant to protection or specific diagnosis or a *Mycoplasma* or are unrelated to the *Mycoplasma*. In addition, other serum/plasma components may interfere with the specific reactions between pathogen components and antibodies to them.

In contrast, the probes described in the present invention are highly enriched in *Mycoplasma*-specific antibodies of particular importance to protective immunity.

It is preferred that the biological samples are taken from the animals at a predetermined time in the development of the disease. In general, for a *Mycoplasma* infection, it has been found that the biological samples should be taken approximately 2 to 7 days after challenge with or after administration of products obtained from a pathogen or with the pathogen itself.

The cells isolated from the biological sample may include B cells.

Thus, preferably the cells are taken a short time after in vivo stimulation, preferably within approximately 2 to 5 days thereafter, resulting in the in vivo induction of antibody forming cells which will secrete specific antibodies into the culture medium after in vitro incubation.

In vitro secretion of antibodies in the culture medium by recently activated B cells may be enhanced by the addition of helper factors to the cultures. The helper factors may be cytokines used alone or in combination, including Interleukin 1, 2, 3, 4, 5, 6, 7 and 8, colony stimulating factors, interferons and any other factors that may be shown to have an enhancing effect on specific B cell secretion.

The method of producing an antibody may include a further step of activating the cells isolated to proliferate and secrete and/or release antibodies.

The cell activation step may include adding a cell activating agent to the culture medium. The cell activating agent may be selected from mitogens and helper factors produced by leukocytes, or their synthetic equivalents or combinations thereof.

The mitogens may be selected from products derived from pokeweed (*Phytolacca americana*) also known as pokeweed mitogen (PWM), polyvinylpyrrolidone (PVP), polyadenylic-polyuridylic acid (poly(A-U)), purified protein derivate (PPD), polyinosinic-polycytidilic acid (poly(I-C)), lipopolysaccharide (LPS), staphylococcal organisms or products thereof, Bacto-streptolysin O reagent (SLO), Staphylococcal phage lysate (SPL), Epstein-Barr virus (EBV), Nocardia water-soluble mitogen (NWEM), phytohemagglutinin (PHA), Concanavalin A (Con A), and dextran-sulphate and mixtures thereof. The cell proliferation agent may be any agent that indirectly or directly results in B cell proliferation and/or antibody secretion such as solid-phase anti-immunoglobulin. The helper factors may be cytokines including interleukin 1, 2, 3, 4, 5, 6, 7 and 8, colony stimulating factors, interferons and any other helper factors that may be shown when added alone, or in combination with other factors and agents, to have an enhancing effect on specific B cell proliferation and/or antibody secretion. This in no way is meant to be an exhaustive list of mitogens and cell actuating agents including helper factors.

The in vitro culturing of the cells may be conducted with or without prior steps to separate sub-populations of cells. The harvesting of antibodies may be conducted by harvesting of the supernatant from the culture medium. This supernatant contains antibodies secreted by these cells during the in vitro culture or artificially released from the B cells, for example by lysis of the B cells. It has been found that the antibody-containing supernatants may be used directly to detect antigens of the *Mycoplasma*.

In a preferred aspect of the present invention, there is provided a method for identifying an antigen associated with a *Mycoplasma*, preferably *Mycoplasma hyopneumoniae*. This method includes providing a sample of a *Mycoplasma*; and an antibody probe including at least one antibody against a *Mycoplasma*;

probing the *Mycoplasma* sample with the antibody probe to detect at least one antigen; and isolating the antigen detected.

Figure 2:
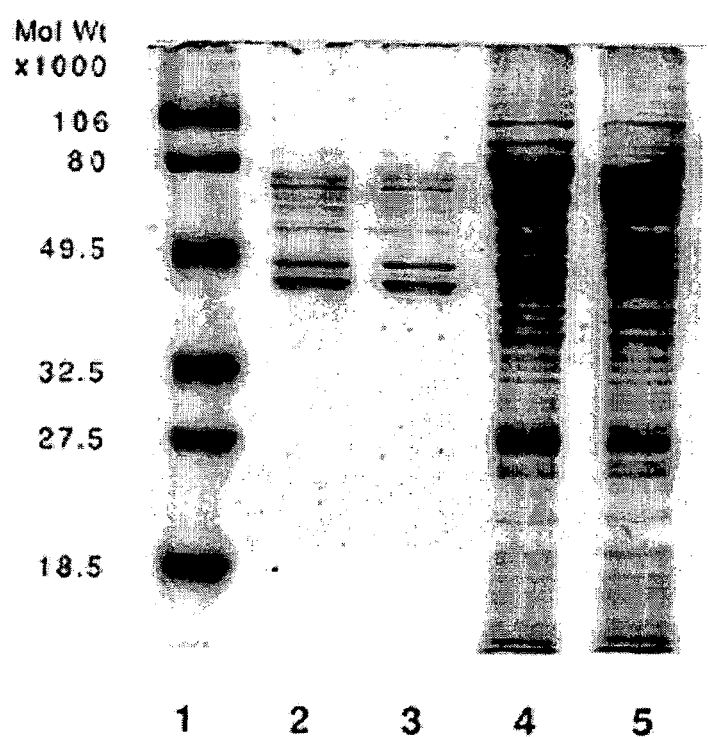

The sample of *Mycoplasma* may be mixed with a standard buffer solution and placed on a standard support such as an SDS-polyacrylamide gel to separate the proteins contained thereon (FIG. 2).

Alternatively, the proteins may be selected utilizing the non-ionic detergent Triton X-114 (TX-114). Insoluble material may be removed by centrifugation. Proteins soluble in the TX-114 phase may then be precipitated out (FIG. 2).

The separate proteins may then be transferred to nitrocellulose, nylon or other sheets.

Figure 3:
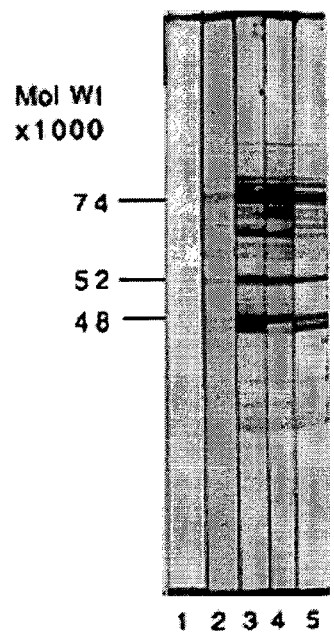
Figure 4:
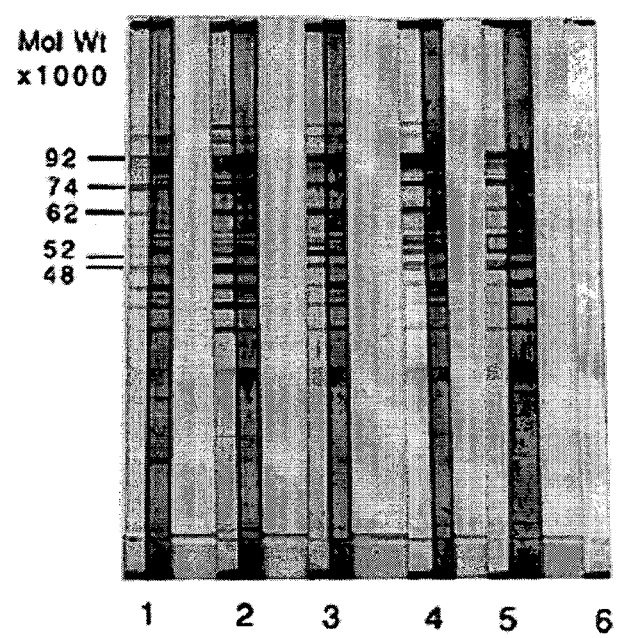
Figure 5:
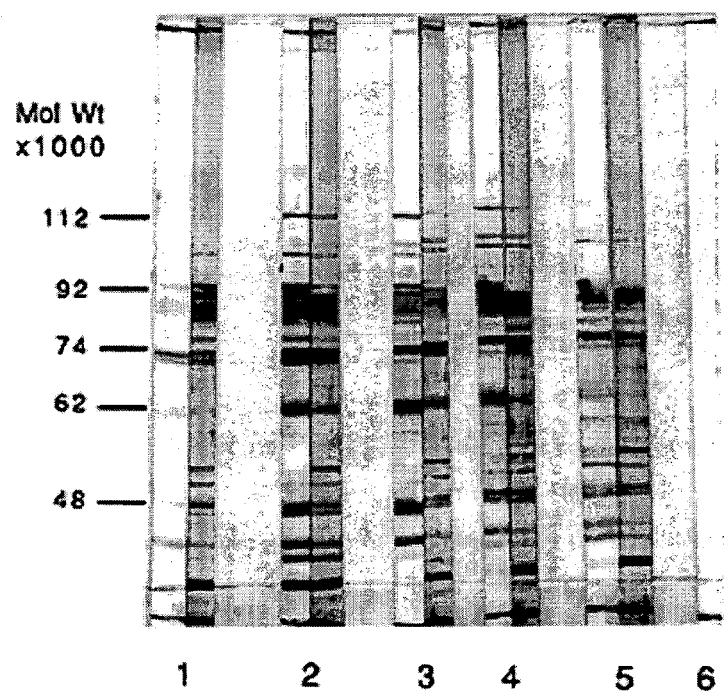

The probing with a suitable antibody may further include subjecting the product produced thereby to a detection assay. The detection assay may include Western blot techniques. The detection assay may be an immunoprecipitation assay, a radioimmunoassay, an enzyme-linked immunoassay or immunofluorescent assay (FIGS. 3, 4 and 5).

The antibody produced as described above may be utilized simply in the form of the supernatant harvested from the culture medium. Alternatively, the antibodies may be separated and purified.

In a further preferred aspect of the present invention the antibody contained in the culture medium may be used for the affinity purification, preferably immuno-affinity purification of antigen.

Accordingly, in a preferred aspect there is provided a method for purifying antigen. This method includes providing a crude antigen mixture; and an antibody against a *Mycoplasma* immobilized on a suitable support;

subjecting the crude antigen mixture to affinity chromatography utilizing the immobilized antibody; and isolating the purified antigen so formed.

The antibody is produced by the method described above.

Antibody can be obtained from the culture supernatant probe by conventional methods. For example, methods usually used to purify immunoglobulins from serum or plasma, e.g. precipitation with ammonium sulphate, fractionation with caprylic acid, ion exchange chromatography, or by binding and elution from immobilized protein G or protein A, may be utilized. Antibody so obtained can then be coupled to suitable supports, e.g., CNBr-activated Sepharose 4B (Pharmacia), Affi-gel (Bio-RAD), or other affinity chromatography supports able to bind proteins.

Immobilized antibody can then be applied to the fractionation and purification of specific antigen from a complex *Mycoplasma* extract by affinity chromatography. After binding of antigen to immobilized antibody, unbound macromolecular species can be washed away from the solid support with, e.g. buffers containing 1.5 M NaCl. Subsequently the antigen can be eluted from the affinity column with, e.g. low or high pH buffer or buffers containing chaotropic ions, e.g. 0.5–3.0 M sodium thiocyanate.

The application of the antibody probe to affinity chromatography enables sufficient quantities of specific antigens to be rapidly isolated from a complex crude extraction mixture for biochemical characterization, amino-acid sequencing and vaccination of animal for limited protection studies. Application of affinity chromatography for obtaining antigen(s) avoids the difficulties often encountered when applying conventional biochemical techniques to the purification of an antigen about which little or no data is known. It also obviates the need to raise polyclonal or monoclonal antibodies for the purpose of "analytical" affinity chromatography. Large scale preparation may, however, require the preparation of polyclonal or monoclonal antibodies.

Having identified the antigen(s) molecular biology, chemical techniques, e.g. cloning techniques, may be used to produce unlimited amounts of this antigen or, alternatively, synthetic peptides corresponding to different fragments of the identified antigens may be used as a means to produce a vaccine.

Accordingly in a preferred aspect of the present invention there is provided a method for preparing a synthetic antigenic polypeptide against *Mycoplasma*, preferably *Mycoplasma hyopneumoniae*, which method includes providing a cDNA library or genomic library derived from a sample of *Mycoplasma*; and an antibody probe as described above;

generating synthetic polypeptides from the cDNA library or genomic library;

probing the synthetic polypeptides with the antibody probe; and isolating the synthetic antigenic polypeptide detected thereby.

Either cDNA or genomic libraries may be used. The cDNA or genomic libraries may be assembled into suitable expression vectors that will enable transcription and the subsequent expression of the clone cDNA, either in prokaryotic hosts (e.g. bacteria) or eukaryotic hosts (e.g. mammalian cells). The probes may preferably be selected from
   (i) synthetic oligonucleotide probes based on the amino acid sequence of the antigen identified and purified as described above;
   (ii) antibodies obtained from the culture medium produced as described above;
   (iii) monoclonal or polyclonal antibodies produced against the antigens identified and purified as described above;
   (iv) recombinant or synthetic monoclonal antibodies or polypeptides with specificity for the antigen, e.g. as described by Ward et al., Nature, 241, pages 544–546 (1989).

The synthetic antigenic polypeptide produced in accordance with the invention may be a fusion protein containing the synthetic antigenic peptide and another protein.

In a further aspect of the present invention there is provided a DNA fragment encoding a putative protective antigen against *Mycoplasma* or related infections, said DNA fragments having a nucleic acid sequence according to FIGS. 6a and 6b or an homologous sequence and functionally active fragments thereof.

In a further preferred aspect of the present invention there is provided a clone including a DNA fragment encoding a putative protective antigen against *Mycoplasma* or related infections, said DNA fragments having a nucleic acid sequence according to FIGS. 6a and 6b or an homologous sequence and functionally active fragments thereof.

Preferably the clone is pC1-2.

The present invention will now be more fully described with reference to the accompanying Examples and drawings. It should be understood, however, that the description following is illustrative only and should not be taken in any way as a restriction on the generality of the invention described above.

IN THE FIGURES

FIG. 1: SDS-Polyacrylamide gel (12.5%) profiles of SDS extracts of species of *Mycoplasma*—Coomassie R250 stained.

| Lane 1 | Pre-stained Molecular Weight Standards |
| Lane 2 | *M. gellisepticum* |
| Lane 3 | *M. synoviae.* |
| Lane 4 | *M. hyopneumoniae.* |
| Lane 5 | *M. hyorhinis.* |
| Lane 6 | *M. flocculare.* |

FIG. 2: SDS-Polyacrylamide gel (12.5%) profiles of extracts of strains of *M. hyopneumoniae*—Coomassie R250 stained gel

| Lane 1 | Pre-stained Molecular Weight Standards. |
| Lane 2 | Triton X-114 extract of *M. hyopneumoniae* - strain Beaufort. |
| Lane 3 | As for Lane 2. |
| Lane 4 | SDS extract of *M. hyopneumoniae* strain Beaufort. |
| Lane 5 | SDS extract of M. *hyopneumoniae* strain 10110. |

FIG. 3: Western blots of Triton X-114 extracted antigens from *M. hyopneumoniae* strain Beaufort, probed with serum and supernatant antibody probes.

| Lane 1 | No antibody control |
| Lane 2 | Dookie pig serum control 1/200. |
| Lane 3 | Pig 105 supernatant. |
| Lane 4 | Pig 1 supernatant. |
| Lane 5 | Dookie pig supernatant. |

FIG. 4: Western blots of SDS extracted antigens from *M. hyopneumoniae* strain Beaufort probed with paired serum and supernatantantibody probes. Fractionation of antigens on SDS Polyacrylamide gel (12.5%).

| Lane 1 | a) Pig 453 supernatant. |
|        | b) Pig 453 serum 1/100. |
| Lane 2 | a) Pig 105 supernatant. |
|        | b) Pig 105 serum 1/100. |
| Lane 3 | a) Pig 1 supernatant. |
|        | b) Pig 1 serum1/100. |
| Lane 4 | a) Pig 15 supernatant. |
|        | b) Pig 15 serum 1/100. |
| Lane 5 | a) Dookie supernatant. |
|        | b) Dookie serum 1/100. |
| Lane 6 | No antibody control. |

FIG. 5: Western blots of SDS extracted antigens from *M. hyopneumoniae* strain Beaufort probed with paired serum and supernatantantibody probes. Fractionation of antigens on SDS Polyacrylamide gel (10.0%).

| Lane 1 | a) Pig 453 supernatant. |
|        | b) Pig 453 serum 1/100. |
| Lane 2 | a) Pig 105 supernatant. |
|        | b) Pig 105 serum 1/100. |
| Lane 3 | a) Pig 1 supernatant. |
|        | b) Pig 1 serum 1/100. |
| Lane 4 | a) Pig 15 supernatant. |
|        | b) Pig 15 serum 1/100. |
| Lane 5 | a) Dookie supernatant. |
|        | b) Dookie serum 1/100. |
| Lane 6 | No antibody control. |

FIG. 6: The entire 48 k gene sequence (SEQ ID NO:1).
FIG. 7: The 48 kDa protein sequence of the 48 k gene sequence (SEQ ID NO:2).

EXAMPLE 1

*Mycoplasma Hyopneumoniae* Media

Friss Media
   Hovind-Hougen, K., Friss, N. F., Research in Veterinary Science, 1991, 51, pp 155–163, "Morphological & Ultrastructural Studies of *M flocculare* and *M hyopneumoniae* in vitro".
   250 ml Hanks BSS
   140 ml Water
   1.5 gm Brain Heart infusion
   1.6 gm PPLO Broth w/o CV
   Autoclave at 120° C. for 20 minutes
   18 ml Yeast Extract (100 g YSC-2 Sigma in 750 ml)
   3.7 ml 0.2% DNA in 0.1% $Na_2CL_3$
   5.14 ml 1%-NAD
   0.6 ml 1% Phenol red Adjust to pH 7.3 to 7.4
Filter through 0.45 um, 0.2 um membrane, store at 4° C.
Add sterile Horse or Pig serum to 20%
and Antibiotics prior to use Etheridge Media Etheridge, J. R., Cottew, G. S., Lloyd, L. C., Australian Veterinary Journal, 1979, August 55, pp 356–359, "Isolation of *Mycoplasma hyopneumoniae* from lesions in experimentally infected pigs".

| Materials | For 600 mls |
|---|---|
| Hanks BSS | 18.9 ml |
| Martleys Digest broth | 1.28 gm |
| Heart Infusion broth | 1.65 gm |
| Lactalbumin hydrolysate | 2.21 gm |
| Glucose | 4.41 gm |
| Yeast Extract autolysate | 8.82 ml |
| Pig Serum (filtered) | 163 ml |
| 1% NAD | 6.17 ml |
| 1% Phenol red | 1.32 ml |
| 0.2% DNA in 0.1% $Na_2CO_3$ | 4.41 ml |

Make up to 600 ml with MQ water (about 350–400 ml)
Adjust pH to 7.4 and filter through: 3.0 um, 0.8 um, 0.45 um, 0.2 um.
Store at 4° C.

Development of Immune Sows

Cull sows and naive gilt (unmated sow designated Dookie).

Challenged on numerous occasions, with culture grown *M. hyopneumoniae* and lung homogenate. Given intranasally and intratracheally. Period of challenge—from September, 1991 to 21st Jan., 1992.

Tiamulin antibiotic given 31st Jan., 1992 to 4th Feb., 1992. Rested for approximately 8 weeks.

Infectious Challenge 120 ml of frozen culture of *M. hyopneumoniae* strain Beaufort, spun down (12,000×g, 20 min.) and resuspended in 50 ml complete medium and cultured overnight at 37° C. The overnight culture was centrifuged (12,000×g, 20 min.) and the mycoplasma cells resuspended in 10 ml serum free mycoplasma culture medium. The 10 ml of concentrated mycoplasma was administered to anaesthetized immune sows via a catheter to ensure the inoculum was placed into the trachea.

Three of four days post-challenge, the sows were killed, and lymph nodes draining the lungs taken—these included the left and right tracheobronchial lymph nodes, and the lymph nodes located at the bifurcation of the trachea.

Antibody probes were prepared from pig lymph nodes and utilized to detect putative protection antigens as described in Australian Patent Application 49035/90 referred to above. Separate cell cultures were obtained from individual lymph nodes. Culture supernatants were harvested after 5 days of culture.

Antigen Preparation

*Mycoplasma hyopneumoniae* strain Beaufort was cultured in Etheridge media until the pH had dropped to between 6.8 and 7.0. Cells of *M. hyopneumoniae* were harvested from culture by centrifugation at 12,000×g for 20 min., washed 4 times with either sterile PBS or 0.25 M NaCl and then the pelleted cells extracted with one of the following.

(i) Sodium Dodecyl Sulphate (SDS)

The cell pellet was resuspended in 0.2% SDS and extracted for 2 hours at 37° C. Insoluble material was pelleted from the extract at 12,000×g for 10 min. and the soluble extract run on SDS-polyacrylamide gel electrophoresis (SDS-PAGE).

(ii) Triton X-114

The method of Bordier (J. Bio. Chem. 1981, 256:1604–1606) was used to selectively extract membrane proteins using the non-ionic detergent Triton X-114.

The cell pellet was resuspended in cold PBS to 2 mg/ml protein and a cold pre-condensed solution of TX-114 added to give a final concentration of 1% (v/v) TX-114. Extraction was achieved by incubation overnight at 4° C. with gentle mixing. Insoluble material was removed by centrifugation at 12,000×g for 20 min. at 4° C. The Triton X-114 soluble membrane proteins were then obtained by achieving a phase separation at 37° C.

Proteins soluble in TX-114 phase were precipitated with 80% ethanol in the presence of carrier dextran (80,000 molecular weight) at −70° C. overnight. The proteins were collected by centrifugation at 12,000×g for 30 min. and dissolved to 500 ug/ml in 4 M urea.

Identification of Antigens

Six antigens were identified utilizing the above-mentioned technique. The identified antigens were those that were consistently identified by the antibody probes from the immune cultures and the Dookie gilt. The results are summarized in Table 1.

TABLE 1

| Molecular Weight (kD) | Characteristics |
|---|---|
| 110–114 | SDS Extracted |
| 90–94 | SDS Extracted |
| 72–75 | Triton X-114 Extracted |
| 60–64** | SDS Extracted. Partitions to aqueous phase of Triton X-114 extract. |
| 52–54 | Triton X-114 Extracted |
| 46–48 | Triton X-114 Extracted |

**Two antigens of approximate molecular weight 62 kD were identified.

| Molecular Weight (kD) | Amino Acid Sequence | |
|---|---|---|
| 46–48 | 48 K N-Terminal: AGXGQTESGSTSDSKPQAETLKHKV | (SEQ ID NO:3): |
| | 48 K CNBR F 1: TIYKPDKVLGKVAVEVLRVLIAKKNKASR | (SEQ ID NO:4): |
| | 48 K CNBR F 2: AEQAITKLKLEGFDTQ | (SEQ ID NO:5): |
| | 48 K CNBR F 3: KNSQNKIIDLSPEG | (SEQ ID NO:6): |
| 52–54 | 52 K Terminal: AGXWAKETTKEEKS | (SEQ ID NO:7): |
| | 52 K CNBR F 1: AWVTADGTVN | (SEQ ID NO:8): |
| | 52 K CNBR F 2: AIVTADGTVNDNKPNQWVRKY | (SEQ ID NO:9): |

-continued

| Molecular Weight (kD) | Amino Acid Sequence | |
|---|---|---|
| 60–64 | 52 K N-Terminal: MKLAKLLKGFX (N/L)(M/V) IK | (SEQ ID NO:10): |
| 60–64 | 52 K N-Terminal: ADP(F/I)(R/E)Y(V/A)PQG(Q/A)X(M/N)VG | (SEQ ID NO:11): |
| 72–75 | 74 K N-Terminal: AGXLQKNSLLEEVWYLAL | (SEQ ID NO:12): |
| | 74 K CNBR F 1: AKNFDFAPSIQGYKKIAHEL | (SEQ ID NO:13): |
| | 74 K CNBR F 2: NLKPEQILQLLG | (SEQ ID NO:14): |
| | 74 K CNBR F 3: LLKAEXNKXIEEINTXLDN | (SEQ ID NO:15): |

CNBR - Cyanogen Bromide fragment.
X denotes an undetermined amino acid.
(A/B) - residue may be A or B PCR of 48 kDa Gene Polymerase Chain Reaction (PCR) oligonucleotide primers were designed from the amino acid sequences obtained from the N-terminal and internal cyanogen bromide (CNBr) derived peptides. Inosine (I) was substituted at positions of high redundancy. The following primers were used in a standard PCR assay, run on a Bartelt Gene Machine Robotic thermal cycling instrument.

```
Oligo 48 K CNBr F 1:    ACIAACGACGAGAAGCCICAGGC
                          T  T   A A         A Oligo 48 K CNBr F 2:    TTIAGCTTIGTGATIGCCTGCTC
                          AT      A     T T
                                  T Oligo 48 K CNBr F 3:    AGGTCGATGATCTTCCAICC
                          AA  A  A T T
                              T  T
```

The resulting PCR products were visualised on a 1.5% agarose gel, excised, and purified using Prep-a-Gene (Bio-Rad). They were cloned by standard techniques into a dideoxy tailed T-vector (Holton and Graham, Nucleic Acids Research 19: 1156, 1991) and the nucleic acid sequence determined. The PCR product, obtained from the reaction using primers F1 and F2 shown above, was of approximately 810 base pairs and was shown by sequencing to code for the previously determined amino acid sequence of the purified native 46–48 kDa protein.

Genomic Clone Isolation of 48 k Gene

The entire 48 K gene has been isolated and sequenced. The gene was obtained from an *M. hyopneumoniae* genomic library made by digesting genomic DNA with the restriction enzyme CLA I and ligating the fragments into the vector pBluescript (Stratagene). The ligated product was then electroporated into *Escherichia coli* strain SURE (Stratagene) and the cells plated on Luria Broth agar plates containing 100 mg/ml Ampicillin (LB-Amp). The library was screened by DNA hybridisation with a polymerase chain reaction (PCR) product specific for the 48 kDa protein. Positive clones were grown in LB-Amp, the cells harvested and the DNA isolated and partially sequenced for confirmation.

The positive clone pC1-2 was entirely sequenced and the protein sequence deduced. This was compared to the protein sequence obtained from the N terminus and Cyanogen Bromide fragments of the 48 kDa protein to show that the gene encoded the desired protein.

Adjuvant Selection

Young piglets, 5–7 weeks of age, were immunized with identified antigen(s). The antigens include Triton X-114 extract and identified proteins of 46–48, 52–53, 60–64, 70–75, 90–94 and 110–114 kD, either singly or in combination. An immunizing dose of antigen, containing between 5–100 μg protein, was given by intramuscular injection in combination with an adjuvant. An adjuvant is selected from (i) Seppic Montanide ISA-50
(ii) Quill A and other derivatives of saponin,
(iii) oil in water emulsion employing a mineral oil such as Bayol F/Arlacel A,
(iv) oil in water emulsion employing a vegetable oil such as corn oil, safflower oil or other with lecithin as emulsifier,
(v) aluminium hydroxide gel, and
(vi) nonionic block polymer such as Pluronic F-127 produced by BASF (U.S.A.).

Immunizing doses were given at 2–4 week intervals, the number of doses being dependent on the adjuvant and amount of antigen, but preferably 2 to 3 doses are given.

Adjuvants were treated on the basis of being able to induce antibody titers, as measured by ELISA, and by assessment of induced cell-mediated immunity as tested by Delayed-Type Hypersensitivity (DTH) reaction.

The results clearly show that mineral-oil type adjuvants are consistently superior at inducing antibody titers and DTH responses (Table 2). In particular an adjuvant marketed under trade designation Montanide ISA-50 and available from Seppic, Paris, France has been found to be suitable.

TABLE 2

| GROUP | Animal Number | DTH 24 Hour Response | DTH 48 Hour Response | Antibody Levels (450 nm) |
|---|---|---|---|---|
| CON- | 19 | 0 | 0 | 0.061 |
| TROL | 11 | 0 | 0 | 0.010 |
| (Un- | 1 | — | — | 0.005 |
| vaccin- | 15 | 0 | 0 | 0.038 |
| nated) | 7 | 0 | 0 | 0.005 |
| QUIL A | 18 | + | 0 | 0.753 |
| | 25 | + | 0 | 0.788 |
| | 17 | 0 | 0 | 0.638 |
| | 168 | — | ± | 0.642 |
| VEG. | 169 | +++ | 0 | 0.316 |
| OIL | 22 | 0 | 0 | 0.621 |
| | 4 | + | 0 | 0.666 |
| | 5 | + | — | 0.239 |
| | 13 | +++ | ++ | 0.457 |
| MIN. | 14 | +++ | ++ | 1.085 |
| OIL | 5 | +++ | ++ | 1.024 |
| | 23 | +++ | + | 0.864 |
| | 15 | +++ | 0 | 0.975 |
| | 21 | + | — | 0.954 |

TABLE 2. Antibody levels and DTH responses in pigs measured 2 weeks after the third injection of antigen from *M. hyopneumoniae*. (— = no response; ± = faint reddening; + = faint reddening and swelling: ++ = reddining: +++ = swelling with or without reddening).

Protection Pen Trial Groups of 9 young piglets, 6 weeks of age, were immunized with purified and semi-purified antigens as shown in Table 3 below. The antigens were purified on reversed-phase HPLC using a formic acid solvent system with an acetonitrile gradient.

Antigens were resolubilized in 4 Molar urea before incorporation in mineral oil adjuvant.

The immunization schedule is as shown in Table 2.

TABLE 3

Protocol for Pen Trial of Antigens of Mycoplasma Hyopneumoniae

| VACCINATIONS & BLEEDS Treatment | Day Number |
|---|---|
| 1st Vaccination | 0 |
| 2nd Vaccination | 14 |
| 3rd Vaccination | 50 |
| Infectious Challenge | 64 |
| Slaughter | 91 |

| ANTIGEN DOSES | |
|---|---|
| Partly Purified | 1st & 2nd Vaccns. 50 µg COMPLEX ANTIGEN/DOSE |
| 52 kD | 3rd Vaccn. - 220 µg PARTIALLY PURIFIED ANTIGEN/DOSE |
| (Purified)74 + 52 kD | 1st Vaccn. 20 µg total protein/DOSE<br>2nd Vaccn. 13 µg total protein/DOSE<br>3rd Vaccn. 17 µg total protein/DOSE |
| (Purified) 48 KD | 1st Vaccn. 20 µg/DOSE<br>2nd Vaccn. 18 µg/DOSE<br>3rd Vaccn. 27 µg/DOSE |

All Protein Estimations Done by "BCA" Protein Assay (Pierce, Ill., U.S.A.

Protection from infection with *Mycoplasma hyopneumoniae* was assessed by infectious challenge 2 weeks after the final immunization. Infectious challenge was achieved by intranasal administration of 10 ml of a 10% (w/v) lung homogenate, prepared from infected lung, and by housing test piglets with previously infected piglets. Four weeks after infectious challenge, the animals were killed and the extent and degree of lung lesions assessed (Table 4).

TABLE 4

Pen Trial of Antigens of Mycoplasma Hyponeumoniae

| Group No. | No. Pneumonia Free (%) | Medium Lung Lesion Score | % Reduction (from Median) |
|---|---|---|---|
| Controls | 1 (11) | 13 | 0% |
| 52 kD | 0 (0) | 5 | 61% |
| 74 ÷ 52 kD | 3 (33) | 6.75 | 48% |
| 48 kD | 2 (22) | 6.25 | 52% |

REFERENCE

Warren H. S. and Chedid, L. A., Future Prospects for Vaccine Adjuvants CRC Critical Reviews in Immunology 8: 83–108, 1988.

Finally, it is to be understood that various other modifications and/or alterations may be made without departing from the spirit of the present invention as outlined herein.

The invention claimed is:

1. An isolated antigen prepared by a method comprising:
   (a) providing a sample of a *Mycoplasma*,
   (b) providing an antibody probe including at least one antibody against the *Mycoplasma*, said at least one antibody being produced by a method comprising
      (i) providing a biological sample taken after a mammal has been challenged with the *Mycoplasma* or an extract comprising the *Mycoplasma* at an infection or lesion site, said biological sample being taken from the infection or lesion site or an area close to the infection or lesion site, wherein the biological sample is taken from the mammal within about 2 to 5 days after the mammal has been challenged with the *Mycoplasma* or extract;
      (ii) isolating antibody producing cells from the biological sample;
      (iii) culturing the isolated cells in vitro in suitable culture medium; and
      (iv) harvesting the at least one antibody from said cultured cells;
   (c) probing the *Mycoplasma* sample with the antibody probe to detect at least one antigen; and
   (d) isolating the at least one antigen detected.

2. An isolated antigen comprising a molecular structure that is identifiable with an antibody probe produced by harvesting an antibody from antibody producing cells of a mammal that are at or close to an infection or lesion site within 2 to 5 days after said mammal is challenged by infection with *Mycoplasma hyopneumoniae* at said infection or lesion site, said molecular structure being a native *Mycoplasma hyopneumoniae* antigen having an approximate molecular weight in kilodaltons (kD) of between 110–114, 90–94, 72–75, 52–54 or 46–48, or being a mutant, derivative or fragment of the native antigen that stimulates production of the antibody in the antibody producing cells, wherein if the molecular structure is the native antigen having the molecular weight between 72–75 kD, the molecular structure contains an N-terminal amino acid sequence comprising SEQ ID NO:12, and wherein if the molecular structure has a molecular weight between 46–48 kD, the molecular structure has an N-terminal amino acid sequence comprising SEQ ID NO:3.

3. An isolated antigen according to claim 2, wherein the molecular structure comprises the N-terminal amino acid sequence comprising SEQ ID NO:12.

4. An isolated antigen according to claim 3, comprising at least one internal amino acid sequence selected from the group consisting of SEQ ID NO13; SEQ ID NO:14 and SEQ ID NO:15.

5. An isolated antigen according to claim 2, wherein the molecular structure has a molecular weight between 60–64 kD and has an N-terminal amino acid sequence comprising SEQ ID NO:10 or SEQ ID NO:11.

6. An isolated antigen according to claim 2, wherein the molecular structure has a molecular weight between 52–54 kD and has an N-terminal amino acid sequence comprising SEQ ID NO:7.

7. An isolated antigen according to claim 6, comprising at least one internal amino acid sequence selected from the group consisting of SEQ ID NO:8 and SEQ ID NO:9.

8. An isolated antigen according to claim 2, wherein the molecular structure has a molecular weight between 46–48 DK and has an N-terminal amino acid sequence comprising SEQ ID NO:3.

9. An isolated antigen according to claim 8, comprising at least one internal amino acid sequence from the group consisting of SEQ ID NO:4; SEQ ID NO:5 and SEQ ID NO:6.

10. A method for preparing a synthetic antigenic polypeptide against *Mycoplasma*, which method comprises
    (a) providing a cDNA library or genomic library derived from a sample of the *Mycoplasma*;
    (b) providing an antibody probe produced by
       (i) providing a biological sample taken after a mammal has been challenged with the *Mycoplasma* or an extract comprising the *Mycoplasma* at an infection or lesion site, said biological sample being taken from the infection or lesion site or an area close to the infection or lesion site, wherein the biological sample is taken from the mammal within about 2 to 5 days after the mammal has been challenged with the *Mycoplasma* or extract;
       (ii) isolating antibody producing cells from the biological sample;
       (iii) culturing the isolated cells in vitro in a suitable culture medium; and
       (iv) harvesting at least one antibody from said isolated cells;
    (c) generating synthetic polypeptides from the cDNA library or genomic library;
    (d) probing the synthetic polypeptides with the antibody probe to detect the synthetic antigenic polypeptide; and
    (e) isolating the synthetic antigenic polypeptide detected thereby.

11. A method according to claim 10, wherein the at least one antibody is raised against an antigen from *Mycoplasma hyopneumoniae* or a related organism, said antigen being selected from the group of native *Mycoplasma* antigens having approximate molecular weights of 110–114, 90–94, 72–75, 52–54 and 46–48 kilodaltons (kD) or being a mutant, derivative or fragment of a native *Mycoplasma* antigen that stimulates production of the at least one antibody in said mammal.

12. A synthetic antigen produced by the method of claim 10.

13. A vaccine or veterinary composition comprising a prophylactically effective amount of at least one antigen according to claim 2.

14. A vaccine or veterinary composition comprising prophylactically effective amounts of a plurality of antigens according to claim 2.

15. A diagnostic kit including an antigen according to claim 2.

16. A method for preventing or treating *Mycoplasma* infection, which method comprises administering to a mammal a prophylactically or therapeutically effective amount of at least one antigen according to claim 2.

17. An amino acid sequence encoded by a SEQ ID NO:1.

18. An amino acid sequence consisting of SEQ ID NO:2.

* * * * *

SEQUENCE LISTING

<160> NUMBER OF SEQ ID NOS: 18

<210> SEQ ID NO 1
<211> LENGTH: 1782
<212> TYPE: DNA
<213> ORGANISM: Mycoplasma hyopneumoniae

<400> SEQUENCE: 1

```
atgaaaaaaa tgccactata ccagaggaaa gagcagtata taaaataatt aaaattacat      60
tttcttcatt tgcgccagaa tttttaagaa ttagtacatt aaaaagtaga acaaaagtta     120
ttaatgtaaa cattagcgca atccttaaga aaaaattaaa agttttatct attttttta     180 atcgaaatcc aaccaggcat aaatctttgt cagtatttat caagtcggta tttttcatt     240 atttctacta aaatattatt tgaatttgca ttttccataa tctaaaattt tacatttttt     300
tataacaatt tttaaaaatt actctttaat ttatagtatt tttttatttt ttagtctaaa     360
ttataaaatt atcttgaatt ttatttgaat tttataatt tagtactaaa aaatacaaat     420
attttttcct attctaagaa aaattcattt tttaaaaaaa attgattttt atagtataat     480
ttgtttgtat aattgaatta acttgatttg aaagggaaca aaatgaaaaa aatgcttaga     540
aaaaaattct tgtattcatc agctatttat gcaacttcgc ttgcatcaat tattgcattt     600
gttgcagcag gttgtggaca gacagaatca ggttcaactt ctgattctaa accacaagcc     660
gagacgctaa aacataaagt aagtaatgat tctattcgaa tagcactaac cgatccggat     720
aatcctcgat gaattagtgc ccaaaaagat attatttctt atgttgatga aacagaggca     780
```

-continued

```
gcaacttcaa caattacaaa aaaccaggat gcacaaaata actgactcac tcagcaagct    840
aatttaagcc cagcgccaaa aggatttatt attgccsctg aaaatggaag tggagttgga    900
actgctgtta atacaattgc tgataaagga attccgattg ttgcctatga tcgactaatt    960
actggatctg ataaatatga ttggtatgtt tcttttgata atgaaaaagt tggtgaatta   1020
caaggtcttt cacttgctgc gggtctatta ggaaaagaag atggtgcttt tgattcaatt   1080
gatcaaatga atgaatatct aaaatcacat atgccccaag agacaatttc tttttataca   1140
atcgcgggtt cccaagatga taataattcc caatatttt ataatggtgc aatgaaagta   1200
cttaaagaat taatgaaaaa ttcgcaaaat aaaataattg atttatctcc tgaaggcgaa   1260
aatgctgttt atgtcccagg atgaaattat ggaactgccg gtcaaagaat ccaatctttt   1320
ctaacaatta acaagatcc agcaggtggt aataaaatca agctgttgg ttcaaaacca   1380 gcttctattt tcaaaggatt tcttgcccca atgatggaa tggccgaaca agcaatcacc   1440
aaattaaaac ttgaagggtt tgatacccaa aaatctttg taactcgtca agattataat   1500
gataaagcca aaactttat caagacggc gatcaaaata tgacaattta taaacctgat   1560
aaagttttag gaaagttgc tgttgaagtt cttcgggttt taattgcaaa gaaaaataaa   1620
gcatctagat cagaagtcga aaacgaacta aaagcaaaac taccaaatat ttcatttaaa   1680
tatgataatc aaacatataa agtacaaggt aaaaatatta atacaatttt agtaagtcca   1740
gtaattgtta caaaagctaa tgttgataat cctgatgcct aa                      1782
```

<210> SEQ ID NO 2
<211> LENGTH: 419
<212> TYPE: PRT
<213> ORGANISM: Mycoplasma hyopneumoniae

<400> SEQUENCE: 2

```
Met Lys Lys Met Leu Arg Lys Lys Phe Leu Tyr Ser Ser Ala Ile Tyr
  1               5                  10                  15

Ala Thr Ser Leu Ala Ser Ile Ile Ala Phe Val Ala Ala Gly Cys Gly
             20                  25                  30

Gln Thr Glu Ser Gly Ser Thr Ser Asp Ser Lys Pro Gln Ala Glu Thr
         35                  40                  45

Leu Lys His Lys Val Ser Asn Asp Ser Ile Arg Ile Ala Leu Thr Asp
     50                  55                  60

Pro Asp Asn Pro Arg Trp Ile Ser Ala Gln Lys Asp Ile Ile Ser Tyr
 65                  70                  75                  80

Val Asp Glu Thr Glu Ala Ala Thr Ser Thr Ile Thr Lys Asn Gln Asp
                 85                  90                  95

Ala Gln Asn Asn Trp Leu Thr Gln Gln Ala Asn Leu Ser Pro Ala Pro
            100                 105                 110

Lys Gly Phe Ile Ile Ala Pro Glu Asn Gly Ser Gly Val Gly Thr Ala
        115                 120                 125

Val Asn Thr Ile Ala Asp Lys Gly Ile Pro Ile Val Ala Tyr Asp Arg
    130                 135                 140

Leu Ile Thr Gly Ser Asp Lys Tyr Asp Trp Tyr Val Ser Phe Asp Asn
145                 150                 155                 160

Glu Lys Val Gly Glu Leu Gln Gly Leu Ser Leu Ala Ala Gly Leu Leu
                165                 170                 175

Gly Lys Glu Asp Gly Ala Phe Asp Ser Ile Asp Gln Met Asn Glu Tyr
            180                 185                 190

Leu Lys Ser His Met Pro Gln Glu Thr Ile Ser Phe Tyr Thr Ile Ala
```

-continued

```
        195                 200                 205

Gly Ser Gln Asp Asp Asn Asn Ser Gln Tyr Phe Tyr Asn Gly Ala Met
    210                 215                 220

Lys Val Leu Lys Glu Leu Met Lys Asn Ser Gln Asn Lys Ile Ile Asp
225                 230                 235                 240

Leu Ser Pro Glu Gly Glu Asn Ala Val Tyr Val Pro Gly Trp Asn Tyr
                245                 250                 255

Gly Thr Ala Gly Gln Arg Ile Gln Ser Phe Leu Thr Ile Asn Lys Asp
            260                 265                 270

Pro Ala Gly Gly Asn Lys Ile Lys Ala Val Gly Ser Lys Pro Ala Ser
        275                 280                 285

Ile Phe Lys Gly Phe Leu Ala Pro Asn Asp Gly Met Ala Glu Gln Ala
    290                 295                 300

Ile Thr Lys Leu Lys Leu Glu Gly Phe Asp Thr Gln Lys Ile Phe Val
305                 310                 315                 320

Thr Arg Gln Asp Tyr Asn Asp Lys Ala Lys Thr Phe Ile Lys Asp Gly
                325                 330                 335

Asp Gln Asn Met Thr Ile Tyr Lys Pro Asp Lys Val Leu Gly Lys Val
            340                 345                 350

Ala Val Glu Val Leu Arg Val Leu Ile Ala Lys Lys Asn Lys Ala Ser
        355                 360                 365

Arg Ser Glu Val Glu Asn Glu Leu Lys Ala Lys Leu Pro Asn Ile Ser
    370                 375                 380

Phe Lys Tyr Asp Asn Gln Thr Tyr Lys Val Gln Gly Lys Asn Ile Asn
385                 390                 395                 400

Thr Ile Leu Val Ser Pro Val Ile Val Thr Lys Ala Asn Val Asp Asn
                405                 410                 415

Pro Asp Ala

<210> SEQ ID NO 3
<211> LENGTH: 25
<212> TYPE: PRT
<213> ORGANISM: Mycoplasma hyopneumoniae
<220> FEATURE:
<221> NAME/KEY: Unsure
<222> LOCATION: (3)
<223> OTHER INFORMATION: Undetermined

<400> SEQUENCE: 3

Ala Gly Xaa Gly Gln Thr Glu Ser Gly Ser Thr Ser Asp Ser Lys Pro
1               5                   10                  15

Gln Ala Glu Thr Leu Lys His Lys Val
            20                  25

<210> SEQ ID NO 4
<211> LENGTH: 29
<212> TYPE: PRT
<213> ORGANISM: Mycoplasma hyopneumoniae

<400> SEQUENCE: 4

Thr Ile Tyr Lys Pro Asp Lys Val Leu Gly Lys Val Ala Val Glu Val
1               5                   10                  15

Leu Arg Val Leu Ile Ala Lys Lys Asn Lys Ala Ser Arg
            20                  25

<210> SEQ ID NO 5
<211> LENGTH: 16
<212> TYPE: PRT
```

-continued

<213> ORGANISM: Mycoplasma hyopneumoniae

<400> SEQUENCE: 5

Ala Glu Gln Ala Ile Thr Lys Leu Lys Leu Glu Gly Phe Asp Thr Gln
              5                  10                  15

<210> SEQ ID NO 6
<211> LENGTH: 14
<212> TYPE: PRT
<213> ORGANISM: Mycoplasma hyopneumoniae

<400> SEQUENCE: 6

Lys Asn Ser Gln Asn Lys Ile Ile Asp Leu Ser Pro Glu Gly
              5                  10

<210> SEQ ID NO 7
<211> LENGTH: 14
<212> TYPE: PRT
<213> ORGANISM: Mycoplasma hyopneumoniae
<220> FEATURE:
<221> NAME/KEY: Unsure
<222> LOCATION: (3)
<223> OTHER INFORMATION: Undetermined

<400> SEQUENCE: 7

Ala Gly Xaa Trp Ala Lys Glu Thr Thr Lys Glu Glu Lys Ser
              5                  10

<210> SEQ ID NO 8
<211> LENGTH: 10
<212> TYPE: PRT
<213> ORGANISM: Mycoplasma hyopneumoniae

<400> SEQUENCE: 8

Ala Trp Val Thr Ala Asp Gly Thr Val Asn
              5                  10

<210> SEQ ID NO 9
<211> LENGTH: 21
<212> TYPE: PRT
<213> ORGANISM: Mycoplasma hyopneumoniae

<400> SEQUENCE: 9

Ala Ile Val Thr Ala Asp Gly Thr Val Asn Asp Asn Lys Pro Asn Gln
              5                  10                  15

Trp Val Arg Lys Tyr
            20

<210> SEQ ID NO 10
<211> LENGTH: 15
<212> TYPE: PRT
<213> ORGANISM: Mycoplasma hyopneumoniae
<220> FEATURE:
<221> NAME/KEY: Unsure
<222> LOCATION: (11)
<223> OTHER INFORMATION: Undetermined
<220> FEATURE:
<221> NAME/KEY: VARIANT
<222> LOCATION: (12)
<223> OTHER INFORMATION: Residue may be Asn or Leu
<220> FEATURE:
<221> NAME/KEY: VARIANT
<222> LOCATION: (13)
<223> OTHER INFORMATION: Residue may be Met or Val

<400> SEQUENCE: 10

Met Lys Leu Ala Lys Leu Leu Lys Gly Phe Xaa Xaa Xaa Ile Lys

-continued

<210> SEQ ID NO 11
<211> LENGTH: 15
<212> TYPE: PRT
<213> ORGANISM: Mycoplasma hyopneumoniae
<220> FEATURE:
<221> NAME/KEY: VARIANT
<222> LOCATION: (4)
<223> OTHER INFORMATION: Residue may be Phe or Ile
<220> FEATURE:
<221> NAME/KEY: VARIANT
<222> LOCATION: (5)
<223> OTHER INFORMATION: Residue may be Arg or Glu
<220> FEATURE:
<221> NAME/KEY: VARIANT
<222> LOCATION: (7)
<223> OTHER INFORMATION: Residue may be Val or Ala
<220> FEATURE:
<221> NAME/KEY: VARIANT
<222> LOCATION: (11)
<223> OTHER INFORMATION: Residue may be Gln or Ala
<220> FEATURE:
<221> NAME/KEY: Unsure
<222> LOCATION: (12)
<223> OTHER INFORMATION: Undetermined
<220> FEATURE:
<221> NAME/KEY: VARIANT
<222> LOCATION: (13)
<223> OTHER INFORMATION: Residue may be Met or Asn

<400> SEQUENCE: 11

Ala Asp Pro Xaa Xaa Tyr Xaa Pro Gln Gly Xaa Xaa Xaa Val Gly
                5                  10                  15

<210> SEQ ID NO 12
<211> LENGTH: 18
<212> TYPE: PRT
<213> ORGANISM: Mycoplasma hyopneumoniae
<220> FEATURE:
<221> NAME/KEY: Unsure
<222> LOCATION: (3)
<223> OTHER INFORMATION: Undetermined

<400> SEQUENCE: 12

Ala Gly Xaa Leu Gln Lys Asn Ser Leu Leu Glu Glu Val Trp Tyr Leu
                5                  10                  15

Ala Leu

<210> SEQ ID NO 13
<211> LENGTH: 20
<212> TYPE: PRT
<213> ORGANISM: Mycoplasma hyopneumoniae

<400> SEQUENCE: 13

Ala Lys Asn Phe Asp Phe Ala Pro Ser Ile Gln Gly Tyr Lys Lys Ile
                5                  10                  15

Ala His Glu Leu
            20

<210> SEQ ID NO 14
<211> LENGTH: 12
<212> TYPE: PRT
<213> ORGANISM: Mycoplasma hyopneumoniae

<400> SEQUENCE: 14

Asn Leu Lys Pro Glu Gln Ile Leu Gln Leu Leu Gly
                5                  10

<210> SEQ ID NO 15
<211> LENGTH: 19
<212> TYPE: PRT
<213> ORGANISM: Mycoplasma hyopneumoniae
<220> FEATURE:
<221> NAME/KEY: Unsure
<222> LOCATION: (6)
<223> OTHER INFORMATION: Undetermined
<220> FEATURE:
<221> NAME/KEY: Unsure
<222> LOCATION: (9)
<223> OTHER INFORMATION: Undetermined
<220> FEATURE:
<221> NAME/KEY: Unsure
<222> LOCATION: (16)
<223> OTHER INFORMATION: Undetermined

<400> SEQUENCE: 15

```
Leu Leu Lys Ala Glu Xaa Asn Lys Xaa Ile Glu Glu Ile Asn Thr Xaa
                  5                  10                  15

Leu Asp Asn
```

<210> SEQ ID NO 16
<211> LENGTH: 23
<212> TYPE: DNA
<213> ORGANISM: Mycoplasma hyopneumoniae
<220> FEATURE:
<221> NAME/KEY: modified_base
<222> LOCATION: (3)
<223> OTHER INFORMATION: primer sequence with modified base: inosine ("i")
<220> FEATURE:
<221> NAME/KEY: modified_base
<222> LOCATION: (18)
<223> OTHER INFORMATION: primer sequence with modified base: inosine ("i")

<400> SEQUENCE: 16

```
acnaacgacg  agaagccnca  ggc                                         23
```

<210> SEQ ID NO 17
<211> LENGTH: 23
<212> TYPE: DNA
<213> ORGANISM: Mycoplasma hyopneumoniae
<220> FEATURE:
<221> NAME/KEY: modified_base
<222> LOCATION: (3)
<223> OTHER INFORMATION: primer sequence with modified base: inosine ("i")
<220> FEATURE:
<221> NAME/KEY: modified_base
<222> LOCATION: (9)
<223> OTHER INFORMATION: primer sequence with modified base: inosine ("i")
<220> FEATURE:
<221> NAME/KEY: modified_base
<222> LOCATION: (15)
<223> OTHER INFORMATION: primer sequence with modified base: inosine ("i")

<400> SEQUENCE: 17

```
ttnagcttng  tgatngcctg  ctc                                         23
```

<210> SEQ ID NO 18
<211> LENGTH: 20
<212> TYPE: DNA
<213> ORGANISM: Mycoplasma hyopneumoniae
<220> FEATURE:
<221> NAME/KEY: modified_base
<222> LOCATION: (18)
<223> OTHER INFORMATION: primer sequence with modified base: inosine -continued

```
("i")
<400> SEQUENCE: 18
aggtcgatga tcttccancc                                              20
```